United States Patent
Reddy et al.

(10) Patent No.: US 10,414,717 B2
(45) Date of Patent: Sep. 17, 2019

(54) PROCESS FOR PREPARING BETA AGONIST

(71) Applicant: VAMSI LABS LTD., Solapur, Maharashtra (IN)

(72) Inventors: G Pratap Reddy, Maharashtra (IN); M. Kesava Reddy, Maharashtra (IN)

(73) Assignee: Vamsi Lab Ltd., Solapur, Maharashtra (IN)

( * ) Notice: Subject to any disclaimer, the term of this patent is extended or adjusted under 35 U.S.C. 154(b) by 0 days.

(21) Appl. No.: 15/750,420

(22) PCT Filed: Aug. 4, 2016

(86) PCT No.: PCT/IN2016/050259
§ 371 (c)(1),
(2) Date: Feb. 5, 2018

(87) PCT Pub. No.: WO2017/021982
PCT Pub. Date: Feb. 9, 2017

(65) Prior Publication Data
US 2019/0055189 A1    Feb. 21, 2019

(30) Foreign Application Priority Data
Aug. 6, 2015 (IN) .................. 2974/MUM/2015

(51) Int. Cl.
| C07C 213/08 | (2006.01) |
| C07C 213/00 | (2006.01) |
| C07C 215/68 | (2006.01) |
| C07C 221/00 | (2006.01) |
| C07C 225/22 | (2006.01) |

(52) U.S. Cl.
CPC .......... *C07C 213/08* (2013.01); *C07C 213/00* (2013.01); *C07C 215/68* (2013.01); *C07C 221/00* (2013.01); *C07C 225/22* (2013.01)

(58) Field of Classification Search
None
See application file for complete search history.

(56) References Cited

FOREIGN PATENT DOCUMENTS

| CA | 1041545 | 10/1978 | |
| CN | 104387284 A | 3/2015 | |
| DE | 3636605 A1 * | 5/1988 | ........... A61K 31/135 |

OTHER PUBLICATIONS 1,4-Dioxane Sigma Aldrich product page, downloaded from https://www.signnaaldrich.com/catalog/product/sia1/296309?lang=en&region=US on Dec. 9, 2018, p. 1-7 (Year: 2018).*

Zou ("Enantioseparations of 11 Amino Alcohols Using Di-n-amyl L-Tartrate-Boric Acid Complex as Chiral Mobile Phase additive by RP-HPLC" Chromatographia, 2015, 78, p. 753-761) (Year: 2015).*

Jiao ("Enantioselective Transport of R-Clenbuterol through a Bulk Liquid Membrane containing O,O'-Dibenzoyl-(2S,3S)-tartaric acid" J. Braz. Chem. Soc., vol. 18, No. 4, 2007, p. 804-809) (Year: 2007).*

International Search Report in PCT/IN2016/050259, dated Sep. 12, 2016.

Wang, et al., "Enantioseparation of Three β-Agonists Using Di-n-butyl d-Tartrate-Boric Acid Complex as Chiral Selector by Means of MEEKC." Chromatographia 75, No. 3-4 (2012): 181-185.

* cited by examiner

*Primary Examiner* — Amy C Bonaparte
(74) *Attorney, Agent, or Firm* — Kilpatrick Townsend & Stockton LLP

(57) ABSTRACT

Disclosed is a process for preparing β-agonist, 1-(4-amino-3,5-dichlorophenyl)-2-(tert-butylamino) ethanol, of Formula I. The process comprises refluxing 1-(4-amino-3,5-dichlorophenyl) ethanone of Formula II and selenium dioxide in the presence of 1,4-dioxane to form compound of Formula III. Further, compound of Formula III is heated at a temperature below 30° C. in the presence of t-butyl amine to form compound of Formula IV. The compound of Formula IV is treated with sodium borohydride to form compound of Formula I.

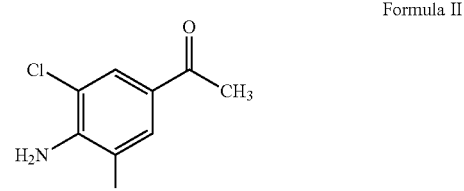

Formula II

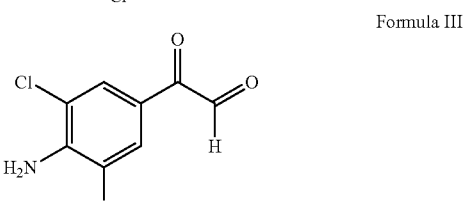

Formula III

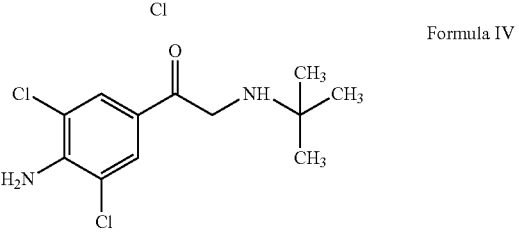

Formula IV

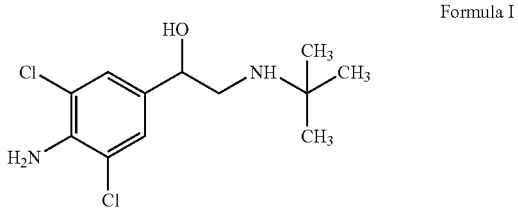

Formula I

10 Claims, No Drawings

PROCESS FOR PREPARING BETA AGONIST

FIELD OF THE INVENTION

The invention relates to a process for preparing β agonist and more particularly, to a process for preparation of Clenbuterol and salts thereof.

BACKGROUND OF THE INVENTION

β-agonists are a class of sympathomimetic agents which act upon the β adrenoceptors that relax muscles of the airways and results in easier breathing.

Clenbuterol (CL) is an extremely potent β-agonist with preferential affinity for β2-adrenoceptor of the bronchial and uterine smooth muscle. Clinical trials have however revealed that the selectivity of CL for bronchodilation is not absolute and even at "therapeutic doses" this β-agonist can activate β1-adrenoceptors in the myocardium (causing palpitation) as well as β2-adrenoceptors in the central nervous system (causing tremors and headaches). (Can Vet J Volume 35, August 1994, 474, http://www.ncbi.nlm.nih.gov/pmc/articles/PMC1686713/pdf/canvetj00357-0012.pdf). The drug is used in the form of oral tablets, granules and dry syrup for the treatment of bronchial asthma in humans in many countries. CL HCl preparations are being used in children as well as adults. Majorly, the drug is being used for veterinary asthma.

U.S. Pat. No. 3,536,712 describes the synthesis of Clenbuterol HCl from 1-(4'amino-phenyl)-2-(t-butyl-amino)-ethanol, hydrogen chloride and chlorine. Other methods use nitro acetophenone or tertiary butyl phenyl ethanol as starting material. In the first method, reduction of nitro group to amino group and chlorination at 3 and 5 positions on the phenyl ring is needed. Also, for addition of the tertiary butylamino group, a bromination step is needed earlier. In the second method, amino group cannot be added directly onto the phenyl ring, nitro group needs to be added, which is then reduced to amino group. Moreover, the process uses phosgene, which is a poisonous gas.

Therefore, there is a need for a process that avoids the use of poisonous materials in the synthesis steps of β-agonists.

SUMMARY OF THE INVENTION

The present invention teaches a process for preparing β-agonist, 1-(4-amino-3,5-dichlorophenyl)-2-(tert-butylamino) ethanol, of Formula I. The process comprises refluxing 1-(4-amino-3,5-dichlorophenyl) ethanone of Formula II and selenium dioxide in the presence of 1,4-dioxane to form compound of Formula III. Further, compound of Formula III is heated at a temperature below 30° C. in the presence of t-butyl amine to form compound of Formula IV. The compound of Formula IV is treated with sodium borohydride at a predefined temperature to form compound of Formula I. The predefined temperature is in a range of 25° C.-30° C.

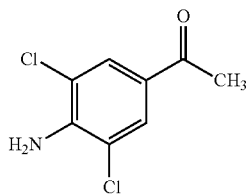

Formula II

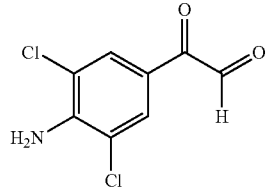

Formula III

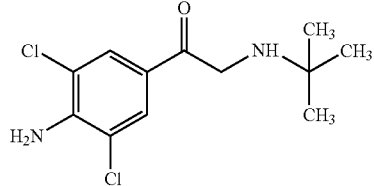

Formula IV

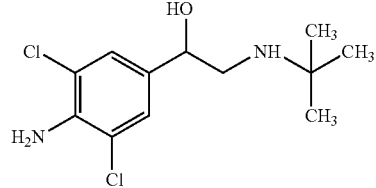

Formula I

In another embodiment the present invention provides a process for preparing β-agonist, (1RS)-1-(4-amino-3,5-dichlorophenyl)-2-(tert-butylamino)ethanol, of Formula VI. The process comprises reacting compound of Formula I with an alcohol in the presence of an activated carbon and tartaric acid to form Clenbuterol tartarate salt of Formula V. The temperature of the reaction is maintained in a range of 25° C.-70° C. Further, compound of Formula V is treated with ammonia solution at a predefined temperature and at a predefined pH to obtain compound of Formula VI. The predefined pH is in a range of 10-12. The predefined temperature is below 30° C.

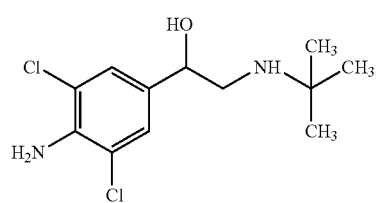

Formula I

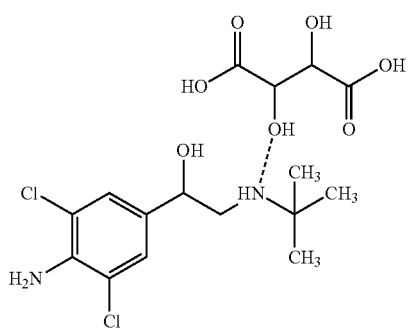

Formula V

Formula VI

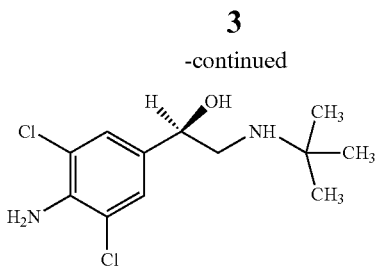

In a preferred embodiment the present invention provides a process for preparing β-agonist, (1RS)-1-(4-amino-3,5-dichlorophenyl)-2-(tert-butylamino) ethanol hydrochloride, of Formula VII. The process comprises treating compound of Formula VI with hydrochloride gas at a predefined temperature and at a predefined pH in the presence of a solvent and activated carbon to form compound of Formula VII. The predefined temperature is in a range of 60°-70° C. The predefined pH is in a range of 6-6.5. The solvent is selected from isopropyl alcohol and toluene. Preferably, the solvent is isopropyl alcohol.

Formula VII

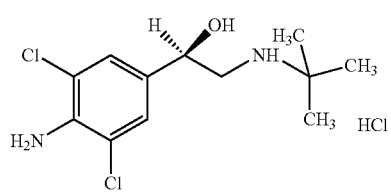

DESCRIPTION OF THE INVENTION

The foregoing objects of the present invention are accomplished and the problems and shortcomings associated with the prior art, techniques and approaches are overcome by the present invention as described below in the preferred embodiments.

An embodiment of the present invention relates to a process for preparing β-agonist, 1-(4-amino-3,5-dichlorophenyl)-2-(tert-butylamino) ethanol, of Formula I. The process comprises refluxing 1-(4-amino-3,5-dichlorophenyl) ethanone of Formula II and selenium dioxide in the presence of 1,4-dioxane to form compound of Formula III. In this step, selenium metal is formed as a by-product.

Further, compound of Formula III is heated at a temperature below 30° C. in the presence of t-butyl amine to form compound of Formula IV. In this step, water is formed as a by-product. The compound of Formula IV is treated with sodium borohydride in the presence of water at a predefined temperature to form compound of Formula I. The predefined temperature is in a range of 25° C.-30° C. In this step, sodium hydroxide and boronic acid are formed as by-products.

The reaction scheme of preparing compound of Formula I is represented below:

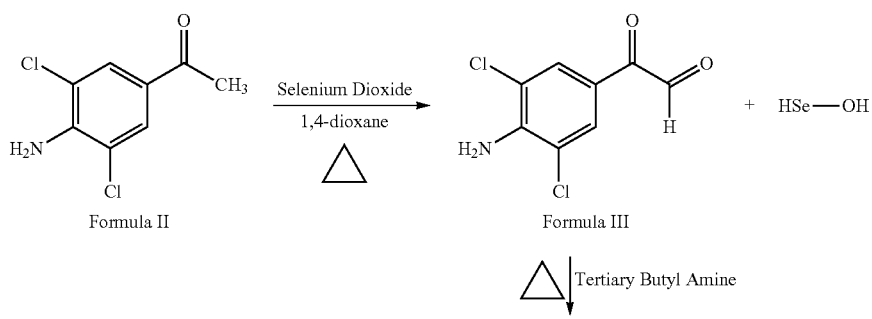

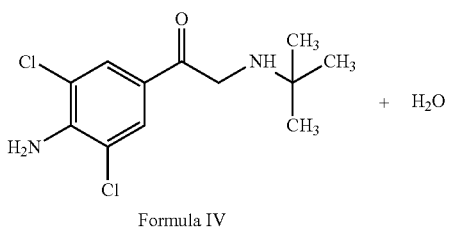

Formula IV

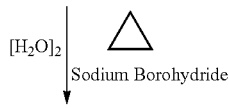

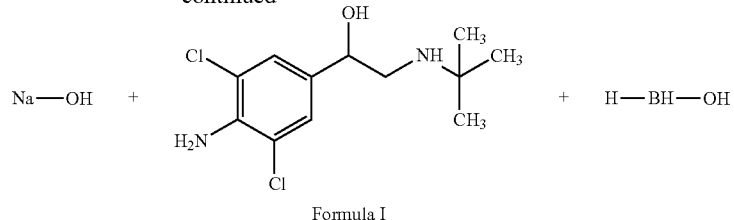

In another embodiment the present invention provides a process for preparing β-agonist, (1RS)-1-(4-amino-3,5-dichlorophenyl)-2-(tert-butylamino)ethanol, of Formula VI. The process comprises reacting compound of Formula I with an alcohol in the presence of an activated carbon and tartaric acid to form Clenbuterol tartarate salt of Formula V. The temperature of the reaction is maintained in a range of 25° C.-70° C. The alcohol used is isopropyl alcohol.

Further, compound of Formula V is treated with ammonia solution at a predefined temperature and at a predefined pH to obtain compound of Formula VI. The predefined pH is in a range of 10-12. The predefined temperature is below 30° C. In this step, poly[amino(oxo) acetic acid, water and hydrogen are formed as by-products.

The reaction scheme of preparing compound of Formula VI is represented below:

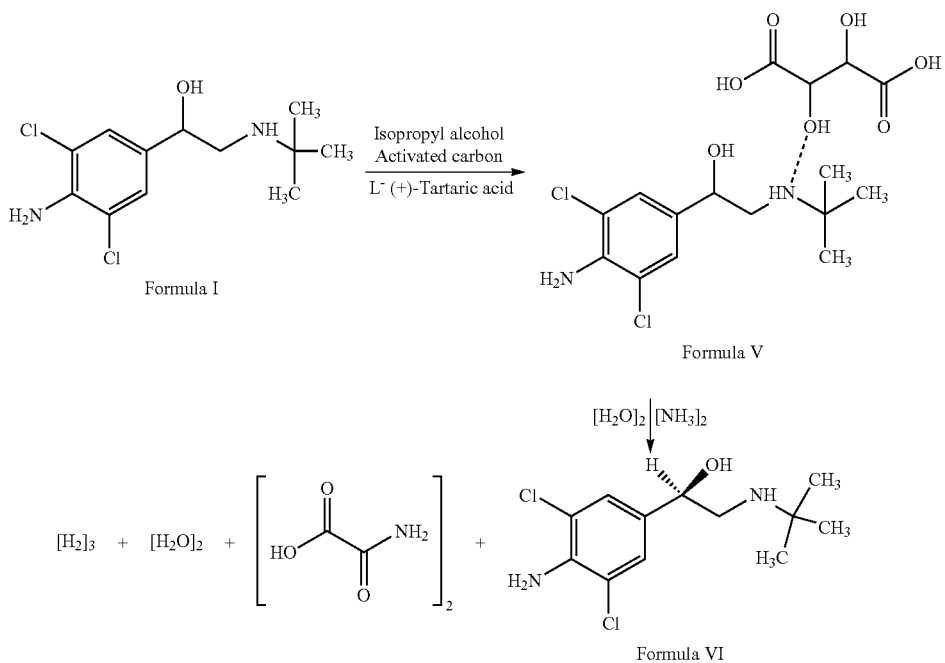

In a preferred embodiment the present invention provides a process for preparing β-agonist, (1RS)-1-(4-amino-3,5-dichlorophenyl)-2-(tert-butylamino) ethanol hydrochloride, of Formula VII. The process comprises treating compound of Formula VI with hydrochloride gas at a predefined temperature and at a predefined pH in the presence of a solvent and activated carbon to form compound of Formula VII. The predefined temperature is in a range of 60° C.-70° C. The predefined pH is in a range of 6-6.5. The solvent is selected from isopropyl alcohol and toluene. Preferably, the solvent is isopropyl alcohol.

The reaction scheme of preparing compound of Formula VII is represented below:

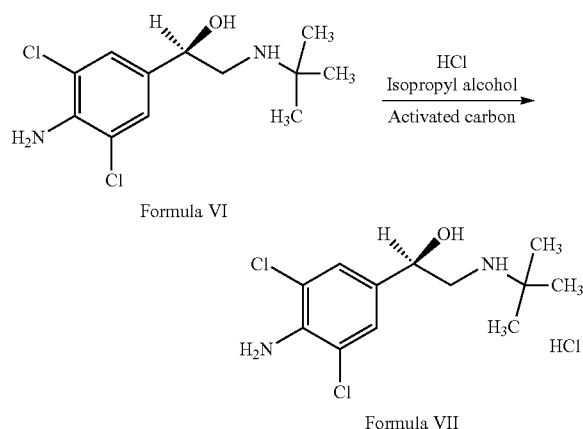

Formula VI

Formula VII

EXAMPLES

The following examples illustrate the invention, but are not limiting thereof.

Example 1

Preparation of 1-(4-amino-3,5-dichlorophenyl)-2-(tert-butylamino) ethanol

A clean and dry reactor was charged with 1,4-dioxane at 25-30° C. To the reactor, 4-amino 2,4-dichloro acetophenone was added followed by selenium dioxide with continuous stirring. The temperature was maintained at 25-30° C. at all times. The mixture was refluxed for 12 hours. Temperature was monitored and recorded every hour. After 12 hours of reflux, the reaction mass was filtered, washed with 1,4-dioxane and the filtrate was cooled to 18-20° C. Tertiary butyl amine was added to the cooled filtrate gradually while maintaining temperature at all times. The reaction was allowed to continue for 2 hours and temperature was monitored every 30 min Completion of reaction was checked with TLC. If the reaction had not proceeded in the desired manner, the reaction was allowed to continue for another hour. Once the reaction was complete, the reaction mixture was cooled to 0-5° C. and then charged with sodium borohydride slowly. The further reaction was carried out at 25-30° C. for 12 hours. Temperature was monitored and recorded every hour. Completion of the reaction was checked with TLC and distilled water was added to the mixture and the precipitate thus formed was filtered through Nutch filter and dried at 50-60° C. to obtain 1-(4-amino-3, 5-dichlorophenyl)-2-(tert-butylamino) ethanol. The formed product was stored in double lined poly bag kept in a HDPE small container.

Example 2

Process for Preparation of (1RS)-1-(4-amino-3,5-dichlorophenyl)-2-(tert-butylamino)ethanol A clean and dry reactor was charged with isopropyl alcohol at 25-30° C. To the reactor, 1-(4-amino-3,5-dichlorophenyl)-2-(tert-butylamino) ethanol obtained in example 1 was added with continuous stirring. The mixture was refluxed for 30 min to check for dissolution. Temperature was monitored every hour up to 4 hours. After 4 hours, activated charcoal was added to the refluxing mixture, stirred for 30 min, filtered through a hypo bed in Bucker funnel and washed with isopropyl alcohol. Tartaric acid was added to the filtrate slowly within 30-40 min at 60-70° C. The mixture was refluxed at 50° C. for 1.5 hours and temperature was monitored every 30 min. The mixture was then filtered through Buckner funnel, washed with isopropyl alcohol and residue was air dried. Distilled water was added to the residue and pH was adjusted to 10-12 using ammonia solution. Mixture was stirred and the temperature was monitored every hour for 3 hours. The mixture was filtered through Buckner funnel and washed with distilled water till pH became neutral. The residue was air dried to obtain (1RS)-1-(4-amino-3,5-dichlorophenyl)-2-(tert-butylamino) ethanol and stored in a double lined poly bag kept in a HDPE small container.

Example 3

Process for Preparation of (1RS)-1-(4-amino-3,5-dichlorophenyl)-2-(tert-butylamino) ethanol hydrochloride A clean and dry reactor was charged with 7.5-10 L of toluene at 25-30° C. To the rector, (1RS)-1-(4-amino-3,5-dichlorophenyl)-2-(tert-butylamino)ethanol obtained in example 2 was added under stirring at 25-30° C. The mixture was heated up to 60-70° C. to dissolve (1RS)-1-(4-amino-3,5-dichlorophenyl)-2-(tert-butylamino)ethanol. Temperature was monitored every 30 min for 1.5 hours after which activated charcoal was added at 60-70° C. and the mixture was further stirred for 1.5 hours. The mixture was filtered and washed with toluene and HCl gas was passed through the mixture at pH 6-6.5 and at 15-20° C. The mixture was stirred at room temperature for 3-4 hours and the temperature was monitored every 30 min. The mixture was filtered through Nutch filter and washed with toluene. The wet cake was charged with isopropyl alcohol/toluene at room temperature, stirred for 1.5 hours, filtered and again washed with isopropyl alcohol/toluene. The final material is air dried to obtain (1RS)-1-(4-amino-3,5-dichlorophenyl)-2-(tert-butylamino) ethanol hydrochloride and stored in double lined poly bag kept in a HDPE small container.

The foregoing description of specific embodiments of the present invention has been presented for purposes of illustration and description. They are not intended to be exhaustive or to limit the present invention to the precise forms disclosed, and obviously many modifications and variations are possible in light of the above teaching.

The embodiments were chosen and described in order to best explain the principles of the present invention and its practical application, to thereby enable others, skilled in the art to best utilize the present invention and various embodiments with various modifications as are suited to the particular use contemplated.

It is understood that various omission and substitutions of equivalents are contemplated as circumstance may suggest or render expedient, but such are intended to cover the application or implementation without departing from the scope of the present invention.

The invention claimed is:

1. A process for preparing β-agonist, (1R)-1-(4-amino-3,5-dichlorophenyl)-2-(tert-butylamino)ethanol or (1S)-1-(4-amino-3,5-dichlorophenyl)-2-(tert-butylamino)ethanol, of Formula I

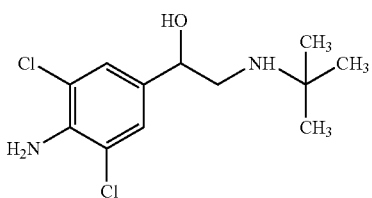

Formula I comprising the steps of:
 a) reacting the (1RS) compound of Formula I with an alcohol in the presence of an activated carbon and tartaric acid at a predefined temperature to form a (1R) or (1S) Clenbuterol tartarate salt of Formula V; and

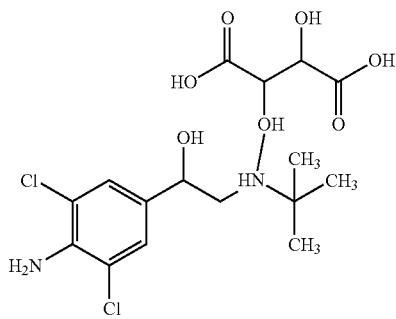

Formula V b) treating a compound of Formula V with an ammonia solution at a predefined temperature and at a predefined pH to form (1R)-1-(4-amino-3,5-dichlorophenyl)-2-(tert-butylamino)ethanol or (1S)-1-(4-amino-3,5-dichlorophenyl)-2-(tert-butylamino)ethanol of Formula I.

2. The process as claimed in claim 1, wherein the predefined temperature in step a) is in a range of 25° C.-70° C.

3. The process as claimed in claim 1, wherein the alcohol used in step a) is isopropyl alcohol.

4. The process as claimed in claim 1, wherein the predefined temperature in step b) is below 30° C.

5. The process as claimed in claim 1, wherein the predefined pH in step b) is in a range of 10-12.

6. The process as claimed in claim 1, further comprising treating the compound (1S)-1-(4-amino-3,5-dichlorophenyl)-2-(tert-butylamino)ethanol of Formula I with hydrochloride gas at a predefined temperature and at a predefined pH in the presence of a solvent and activated carbon to form a compound of Formula VII

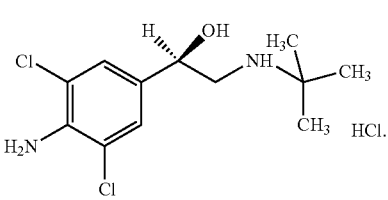

Formula VII

7. The process as claimed in claim 6, wherein the predefined temperature for hydrochloride gas treatment is in a range of 60°-70° C.

8. The process as claimed in claim 6, wherein the predefined pH for hydrochloride gas treatment is in a range of 6-6.5.

9. The process as claimed in claim 6, wherein the solvent is selected from isopropyl alcohol and toluene.

10. The process as claimed in claim 9, wherein the solvent is isopropyl alcohol.

* * * * *